United States Patent [19]
Chapman et al.

[11] Patent Number: 5,772,662
[45] Date of Patent: Jun. 30, 1998

[54] FEMORAL FIXATION SYSTEM

[75] Inventors: Michael W. Chapman, Sacramento, Calif.; Charles C. Edwards, Baltimore, Md.; Dana C. Mears, Oakmont, Pa.

[73] Assignee: Howmedica Inc., New York, N.Y.

[21] Appl. No.: 761,476

[22] Filed: Dec. 6, 1996

Related U.S. Application Data

[60] Continuation of Ser. No. 301,210, Sep. 19, 1994, abandoned, which is a division of Ser. No. 948,193, Sep. 21, 1992, Pat. No. 5,364,398, which is a division of Ser. No. 670,839, Mar. 18, 1991, Pat. No. 5,190,544, which is a division of Ser. No. 232,188, Aug. 15, 1988, Pat. No. 5,041,114, which is a division of Ser. No. 877,626, Jun. 23, 1986, Pat. No. 4,776,330.

[51] Int. Cl.$^6$ ..................................................... A61B 17/80
[52] U.S. Cl. ................................................ 606/69; 606/73
[58] Field of Search ................................ 606/69, 70, 71, 606/60, 54, 53, 73, 72, 76, 86, 101, 105

[56] References Cited

U.S. PATENT DOCUMENTS

| | | | |
|---|---|---|---|
| 1,105,105 | 7/1914 | Sherman | 606/69 X |
| 2,780,223 | 2/1957 | Haggland | 606/69 X |
| 3,463,148 | 8/1969 | Treace | 606/69 X |
| 3,695,259 | 10/1972 | Yost | 606/69 X |
| 3,741,205 | 6/1973 | Markolf et al. | 606/69 X |
| 4,219,015 | 8/1980 | Steinemann | 606/69 X |
| 4,263,904 | 4/1981 | Judet | 606/69 X |
| 4,429,690 | 2/1984 | Angelino-Pievani | 606/69 X |
| 4,655,203 | 4/1987 | Törmälä et al. | 606/69 X |

FOREIGN PATENT DOCUMENTS

| | | | |
|---|---|---|---|
| 2556583 | 6/1985 | France | 606/69 |

*Primary Examiner*—Guy V. Tucker
*Attorney, Agent, or Firm*—Peter C. Richardson; Lawrence C. Akers; Elizabeth O. Slade

[57] ABSTRACT

A modular femoral internal implant system for use in the treatment of femoral disorders resulting from injury, disease or congenital defect includes at least three interconnectable components: 1) an elongated epiphyseal/metaphyseal implant, 2) an intramedullary rod and 3) an angled side plate having an elongated plate portion adapted to be secured to the outer cortical wall and a hollow sleeve adapted to extend into the femur. The epiphyseal/metaphyseal implant can be connected to either the angled side plate or the intramedullary rod. The system may also include an elongated bone plate connectable to the angled side plate, one or more additional epiphyseal/metaphyseal implants of variable length, an additional angled side plate, a distal buttress plate connectable to the elongated bone plate, and a plurality of bone screws of a universal design. Preferably, many or all of the components of the system are made of an inert, resilient titanium-base alloy.

5 Claims, 6 Drawing Sheets

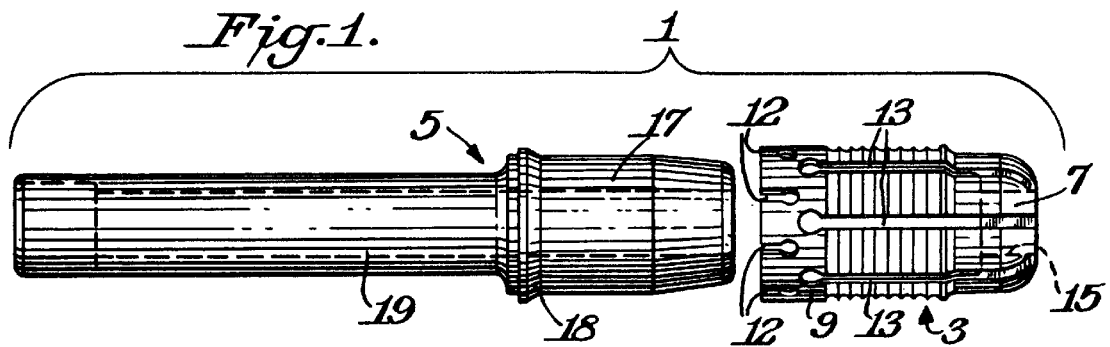
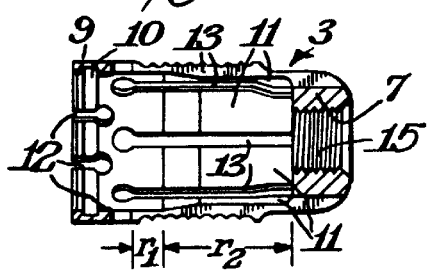
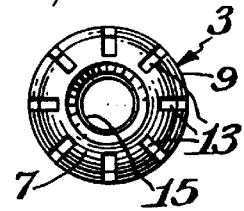
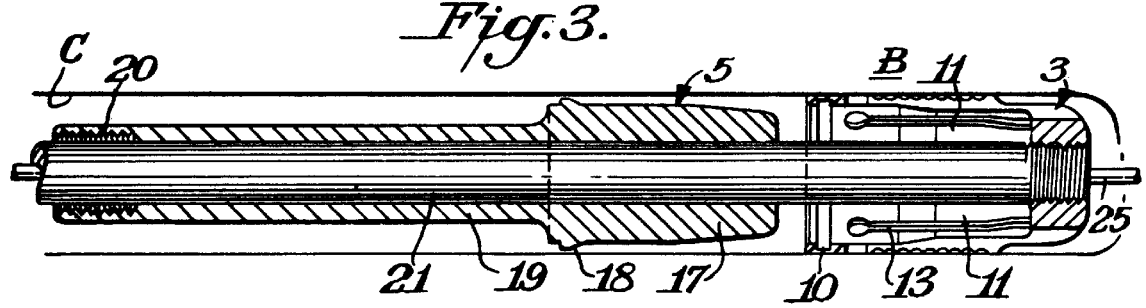
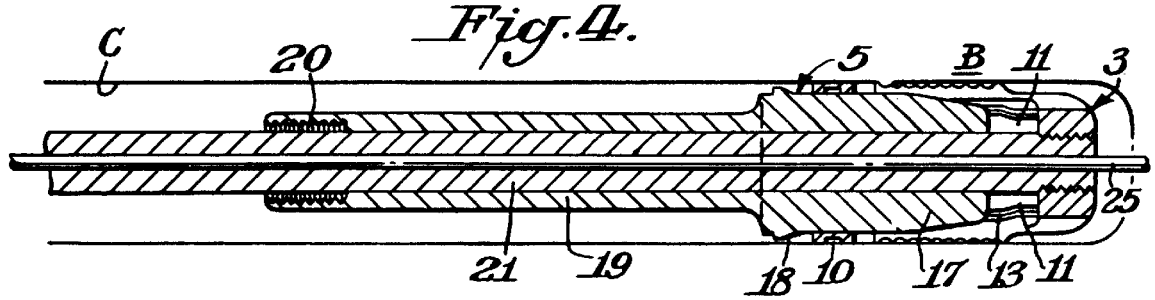
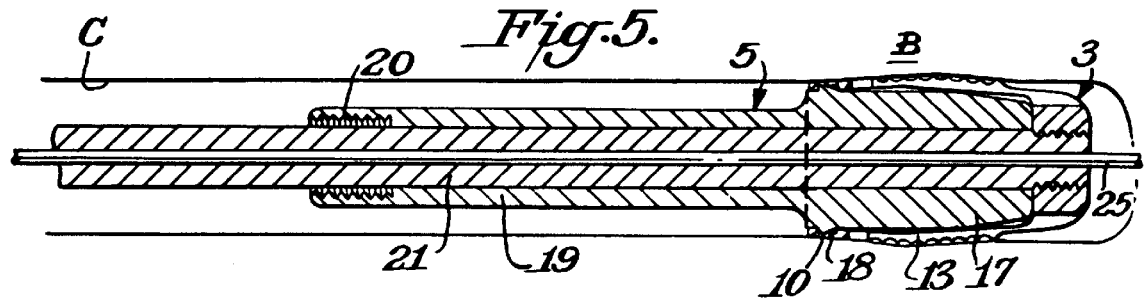

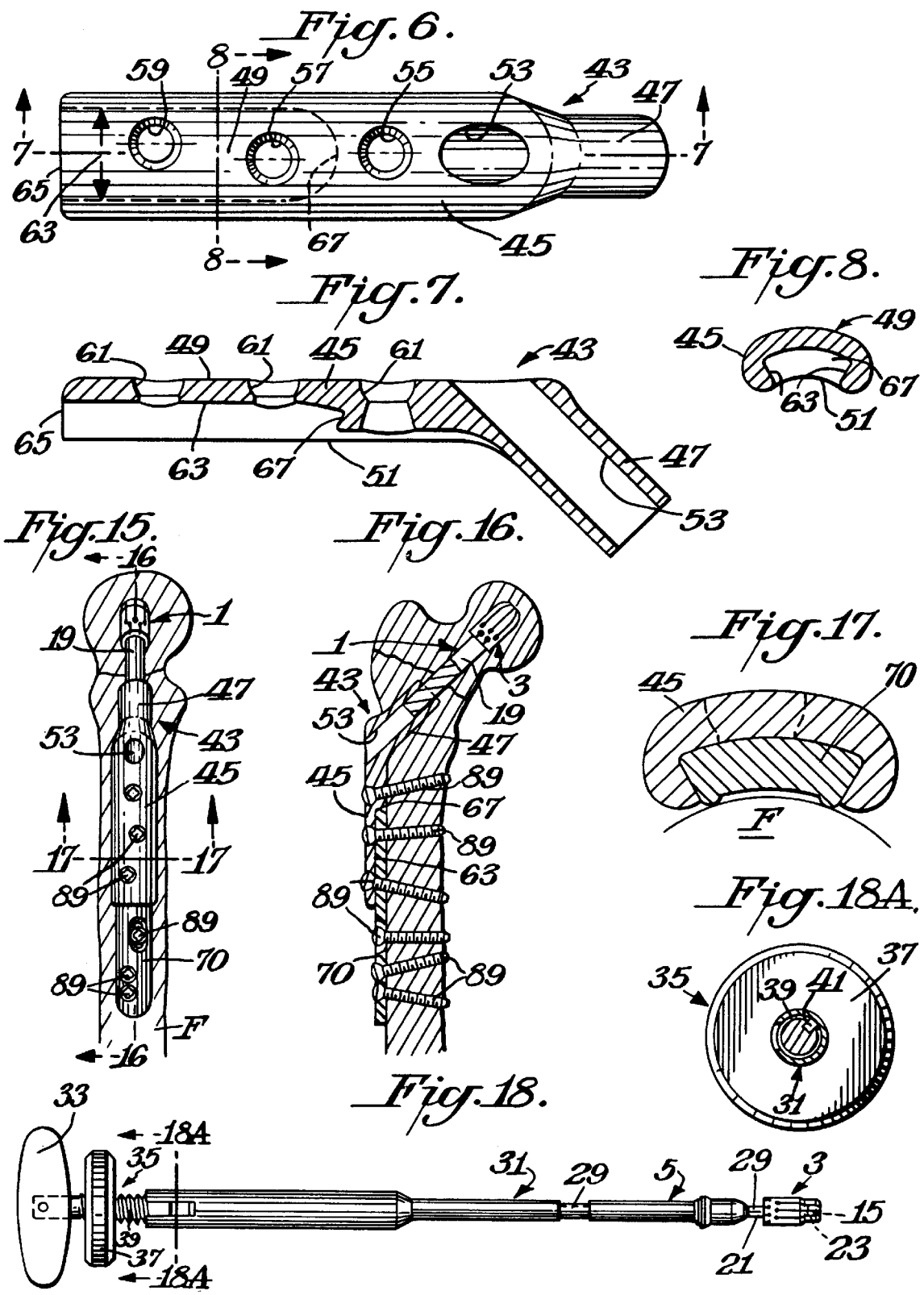

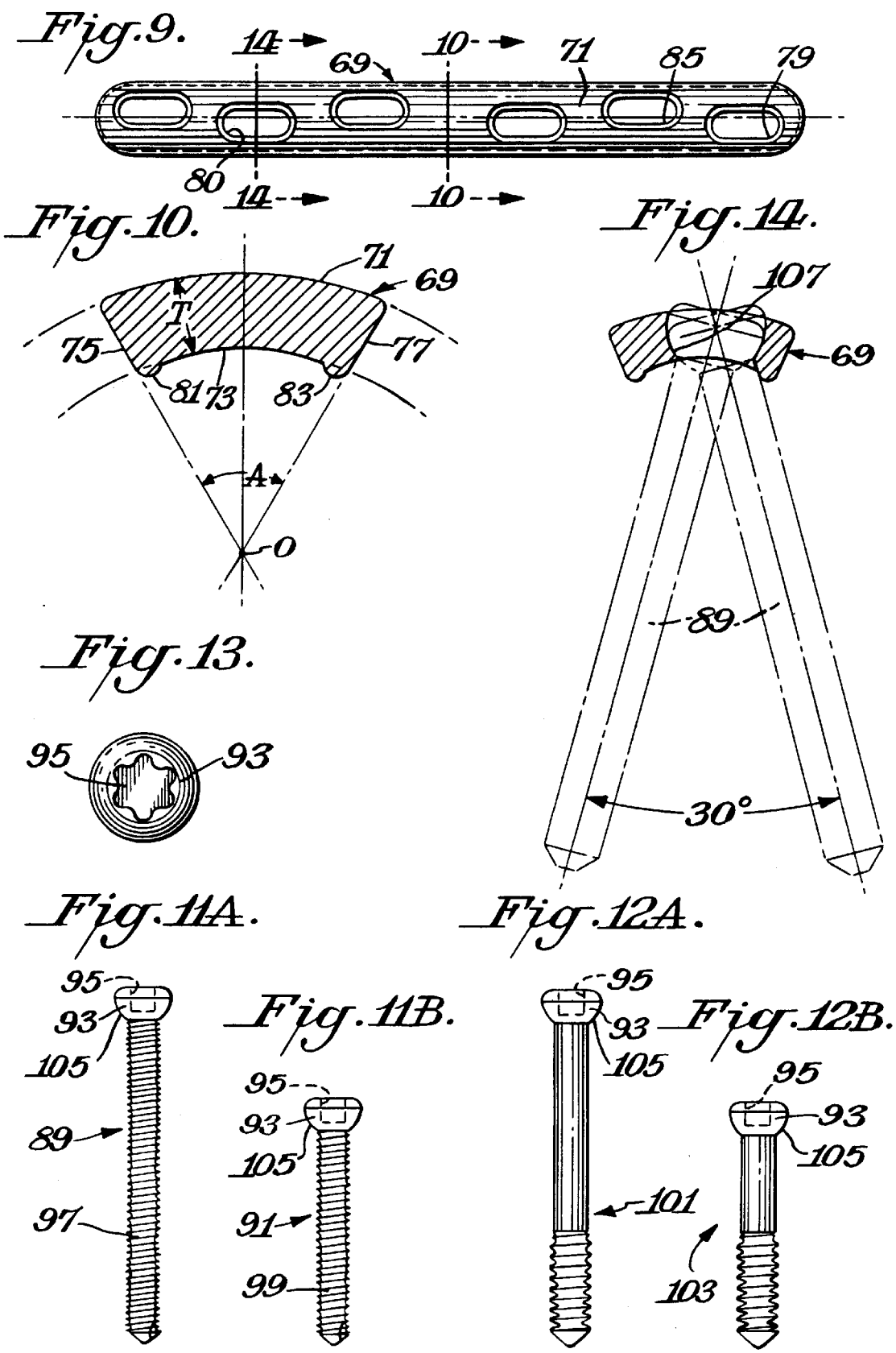

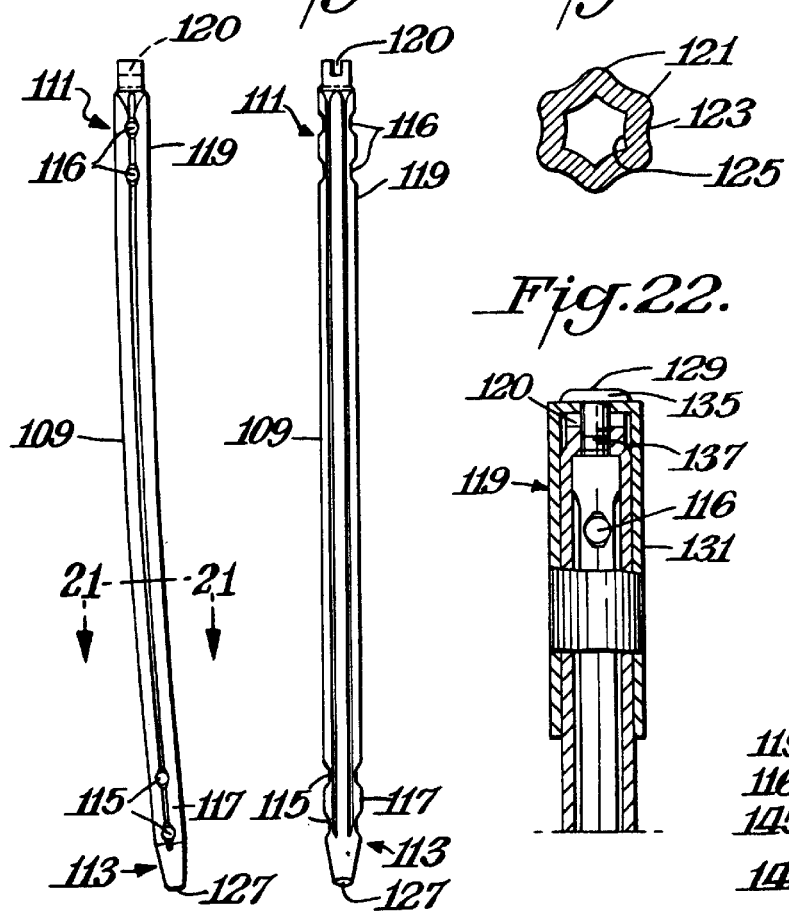

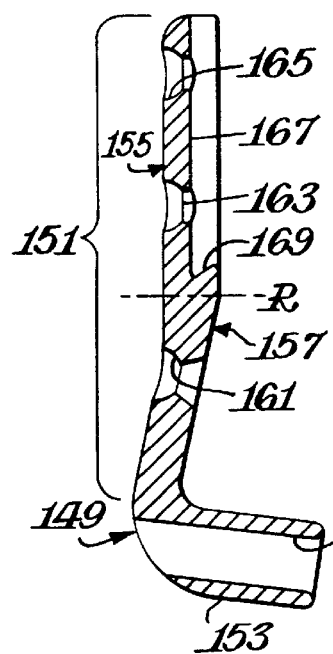
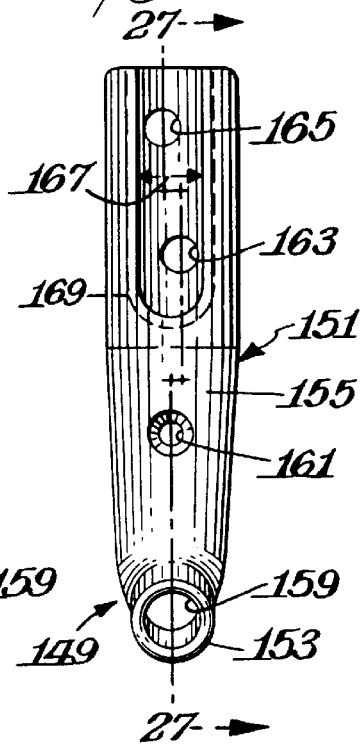
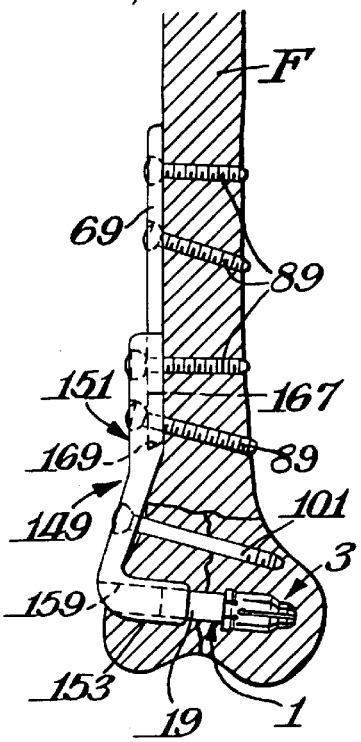
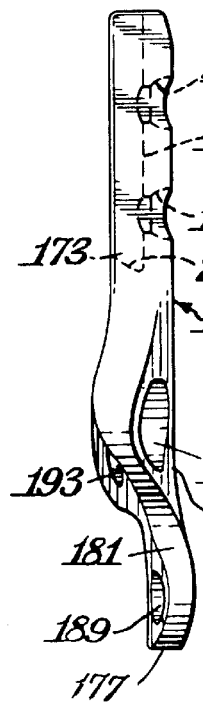
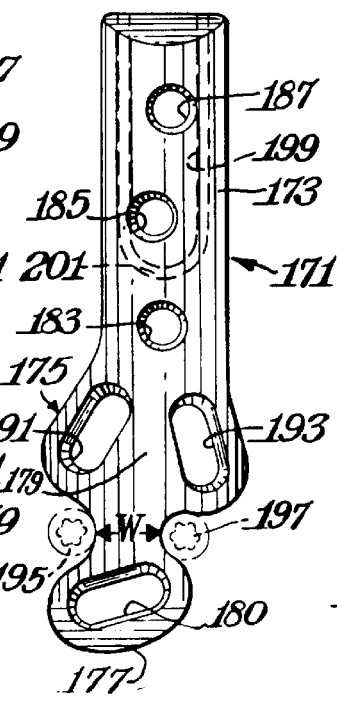
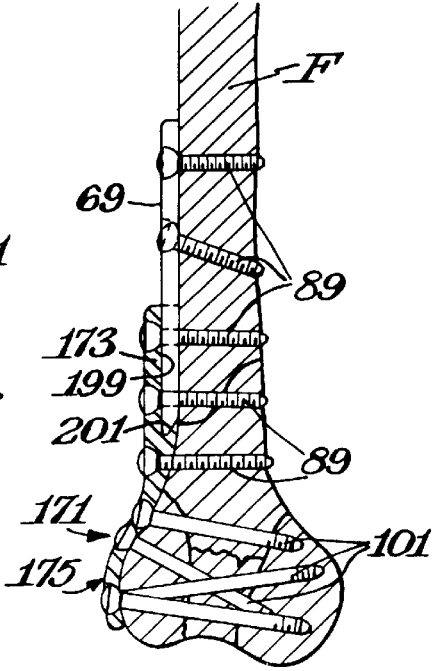

FEMORAL FIXATION SYSTEM

This is a continuation of application Ser. No. 08/301,210 filed on Sep. 6, 1994, now abandoned, which is a division of application Ser. No. 07/948,193, filed on Sep. 21, 1992, now U.S. Pat. No. 5,364,399, which is a division of application Ser. No. 07/670,839, filed on Mar. 18, 1991, now U.S. Pat. No. 5,190,544 which in turn is a division of application Ser. No. 07/232,188, filed on Aug. 15, 1988 (now U.S. Pat. No. 5,041,114), which in turn is a division of application Ser. No. 06/877,626, filed on Jun. 23, 1986, (now U.S. Pat. No. 4,776,330).

BACKGROUND OF THE INVENTION

Internal fixation of femoral fractures is one of the most common orthopedic surgical procedures. Many different types of femoral fractures are encountered in practice, including fractures in the femoral neck, intertrochanteric, mid-shaft and distal condylar regions. The femoral bone will sometimes fracture cleanly into two large fragments along a well-defined fracture line, and on other occasions fracture into many smaller fragments. Often, more than one type of fracture will exist concurrently in different regions of the femur of an injured patient.

A wide variety of implants have been developed over the years for use in the internal fixation of femoral fractures. Although numerous excellent design achievements have been realized, several general problem areas remain. First, almost all of the currently available implants have a highly specialized application limited to only one specific anatomical location in the femur. Thus, a hospital must maintain at great expense a very large and variegated inventory of different implants to handle all expected contingencies. These implants are generally not compatible, i.e. they cannot be interconnected together in case of a complicated fracture, pattern extending into different anatomical regions of the femur. Second, each implant has its own peculiar attributes and deficiencies, and the use of many of the known implants involves the use of a surgical technique that is unique to that implant and sometimes complicated and difficult as well. Consequently, the opportunities for improper implant selection and surgeon error during implantation are inevitably increased. Finally, tissue reactions with implants made of stainless steel and certain other surgical implant alloys tend to reduce the useful lifetime of the implants and require premature removal from the patient's body.

One very commonly utilized femoral internal fixation device is an elongated implant (nail, screw, pin, etc.) adapted to be positioned along the longitudinal axis of the femoral neck with its leading end portion in the femoral head so as to stabilize a fracture of the femoral neck. The elongated implant may be implanted by itself or connected to another implant such as a side plate or intramedullary rod. The leading end portion of the implant typically includes means to positively grip the femoral head bone (external threads, expanding arms, etc.), but the inclusion of such gripping means can introduce several significant problems. First, implants with sharp edges on the leading end portion, such as the externally threaded implants, exhibit a tendency to migrate proximally towards the hip joint bearing surface after implantation. Such proximal migration under physiological loading, which is also referred to as femoral head cut-out, can lead to significant damage to the adjacent hip joint. Also, the externally threaded implants can generate large stress concentrations in the vicinal bone during implantation which can lead to stripping of the threads formed in the bone and thus obviously a weakened grip. The movable arms of known expanding arm devices are usually free at one end and attached at the other end to the main body of the leading end portion of the implant. As a result, all fatigue loading is concentrated at the attached ends of the arms and undesirably large bending moments are realized at the points of attachment.

As stated above, known elongated implants used to stabilize fractures of the femoral neck are often connected in use to a side plate which in turn is secured to the outer cortical wall of the adjacent femoral shaft, for example with bone screws. This type of assembly is often selected when a femoral neck fracture is a part of a more complicated fracture pattern including also one or more fractures in the metaphyseal and/or diaphyseal regions of the femur. Clearly, the surgeon desires to be able to select the appropriate length of the side plate depending upon the particular traumatic condition of the patient's femur. However, the surgeon's flexibility in this regard typically requires the hospital to maintain a costly inventory of implants.

SUMMARY OF THE INVENTION

It is an object of the present invention to provide a modular system of femoral internal implants, and instrumentation therefor, that can be employed to treat a number of different fracture patterns and other disorders with a minimal number of interconnectable system components involving simple uncomplicated operational procedures in which surgical invasiveness and operation times are minimized.

This and other objects of the invention are achieved with a novel kit for use in the amelioration of a number of different types of femoral disorders resulting from injury, disease or congenital defect with a minimal number of interconnectable components. The kit comprises at least the following components: 1) an elongated epiphyseal/metaphyseal implant having a leading end portion and a trailing end portion and adapted to grip bone at its leading end portion; 2) an intramedullary rod having a distal end and a proximal end; 3) an angled side plate comprising an elongated plate portion adapted to be secured to the outer cortical wall of the femoral shaft and an integral hollow sleeve extending at an angle from one end of the plate portion so that said hollow sleeve extends into the femur when the plate portion is secured to said cortical wall; and 4) means for connecting the epiphyseal/metaphyseal implant to the intramedullary rod adjacent to one of the ends of the rod with the epiphyseal/metaphyseal implant at an angle with respect to the intramedullary rod.

According to the invention, the components of the novel kit are dimensioned such that the elongated epiphyseal/metaphyseal implant is capable of being connected to the angled side plate by the insertion of the trailing end portion of the epiphyseal/metaphyseal implant into the hollow sleeve of the angled side plate and the elongated epiphyseal/metaphyseal implant is also capable of being connected to the intramedullary rod with the use of said connecting means. Thus the same epiphyseal/metaphyseal implant can be either connected to the intramedullary rod, to form for example a Y-nail type of assembly to treat an unstable subtrochanteric fracture pattern, or connected to the angled side plate, to form for example a side plate-pin assembly to treat a different fracture pattern. The intramedullary rod may be either connected to the elongated epiphyseal/metaphyseal implant or implanted independently of said implant and the angled side plate.

The novel kit can be used to treat a variety of trauma conditions as well as to ameliorate other types of femoral disorders including non-unions, congenital deformities and pathological deformities (e.g. Paget's disease), and can also be utilized in the prophylactic fixation of weakened bone, bone defects, etc., and in the performance of osteotomies. Simple and uncomplicated surgical techniques can be employed and operating times and implant inventories kept at a low level.

As used herein the term "elongated epiphyseal/metaphyseal implant" refers to an elongated implant adapted to be used in such a manner that it extends after implantation from the epiphyseal region of the proximal femur into the adjacent metaphyseal region, or from the lateral to the medial epiphyseal region of the distal femur. In general, the elongated epiphyseal/metaphyseal implant can be a pin, nail, screw, etc. Preferably, the intramedullary rod is axially cannulated and is provided with at least one through bore adjacent its distal end for reception of a locking screw.

The modular femoral implant system advantageously includes components additional to the essential epiphyseal/metaphyseal implant, intramedullary rod, angled side plate and epiphyseal/metaphyseal implant-intramedullary rod connection means. Thus, the kit preferably includes an elongated bone plate adapted to be secured to the outer cortical wall of the femoral shaft. The elongated bone plate and angled side plate are dimensioned such that the elongated bone plate can be connected to the plate portion of the angled side plate to provide an extension of the effective length of said plate portion without having to inventory two complete angled side plates. The elongated bone plate can of course be utilized by itself in a conventional manner, if desired. Most preferably, several elongated bone plates of variable length are included in the kit.

In a further preferred embodiment of the invention the kit includes a distal buttress plate including a relatively flat elongated proximal portion adapted to be secured to the lateral distal femoral shaft and a relatively curved distal portion adapted to be secured to the lateral distal femoral condyle. In this embodiment the kit includes at least one elongated bone plate that is capable of being connected to each of the plate portion of the angled side plate and the proximal portion of the distal buttress plate for effective length extension purposes, as desired.

The novel kit of the present invention preferably includes a plurality of threaded self-tapping cortical bone screws for use in securing the elongated plate portion of the one or more angled side plates to the outer cortical wall of the femoral shaft and, when the kit includes an intramedullary rod with a distal through bore and one or more elongated bone plates, securing the distal end of the intramedullary rod to the distal femur, securing said bone plate(s) to the outer cortical wall of the femoral shaft, and connecting said plate portion(s) and bone plate(s) together in axial alignment. The kit preferably includes a plurality of such screws each having a head and a threaded shank, with said screws being identical except for variations in the length of the threaded shanks. Although not every one of these screws can be used in all of the capacities set forth above (for example short cortical screws cannot be used to secure the distal end of the intramedullary rod), the provision of a plurality of threaded self-tapping cortical bone screws of universal screw head and screw shank design (except for variations in screw shank length) provides substantial opportunities for interchangeability in use and reduced inventory levels, and requires the surgeon to be familiar with only one set of cortical screw characteristics, attributes and techniques of use. Furthermore, said bone screws can be used independently as bone fixation screws to hold fragments of bone together during healing of a fracture. Most preferably, the heads of the cortical screws and the apertures in the plate portion(s) and bone plate(s) intended to receive them are configured in such a manner that the screws are capable of a universal rotation with respect to the plate portion or bone plate within a cone having an apex angle of at least about 20° when the screw head is fully advanced into the aperture receiving it. Thus, for example, the underside of the universal screw head may be spherically rounded (convex towards the bone) and the abutting surfaces of the screw-receiving apertures complimentary thereto (and of course concave away from the bone).

Preferably, the components of the novel kit of the invention are made of a resilient, physiologically inert titanium-base alloy such as Ti-11.5Mo-6Zr-4.5Sn, Ti-6Al-4V or Ti-3Al-2.5V. The physiological inertness of such alloys reduces the potential for adverse tissue reactions (as compared to e.g. stainless steel) and thus will serve to increase product lifetime in vivo after implantation. Also, most of the currently available implants for the internal fixation or amelioration of femoral fractures or other disorders are made of highly rigid materials, thus leading in many circumstances to excessive "stress shielding" in which too much of the stresses applied to the femur are borne by the implant rather than the healing bone in the fracture region. Stress shielding may delay fracture healing and weaken the surrounding bone. This problem of stress shielding is greatly alleviated by making the components of the kit out of a resilient titanium-base alloy.

In a preferred distribution of components, the kit comprises: 1) two epiphyseal/metaphyseal implants of different length, 2) an angled side plate in which the hollow sleeve and plate portion are mutually oriented at an oblique angle so that the hollow sleeve is adapted to extend into the intertrochanteric region when the plate portion is secured to the outer cortical wall of the adjacent femoral shaft, 3) an angled side plate in which the hollow sleeve and plate portion are substantially perpendicular so that the hollow sleeve is adapted to extend into the distal condylar region of the femur when the plate portion is secured to the outer cortical wall of the adjacent distal femoral shaft, 4) an intramedullary rod (preferably having a through bore adjacent its distal end), 5) means for connecting the shorter of the two epiphyseal/metaphyseal implants to the intramedullary rod adjacent to the proximal end of the rod to form a Y-nail type of assembly, 6) a plurality of cancellous and cortical bone screws, and 7) at least one elongated bone plate capable of being connected in axial alignment to the plate portion of each of the angled side plates for effective length extension purposes. The shorter epiphyseal/metaphyseal implant is also capable of being connected to the substantially perpendicularly-angled side plate, while the longer epiphyseal/metaphyseal implant is capable of being connected to the obliquely-angled side plate. With this highly preferred distribution of components, the components of the kit can be assembled together in different ways or used independently to treat or ameliorate most of the femoral fracture conditions and other femoral disorders commonly encountered by orthopedic surgeons.

In addition to the overall modular concept of the femoral implant system, the present invention is also directed to the particular design of various of the components of the system. Thus, included within the concept of the present invention is a novel bone implant for use in the stabilization of a bone fracture comprising an integral substantially cylindrical expansion sleeve having a smoothly rounded circumferentially-closed dome at one end, a circumferentially-closed circular ring at its other end, and a plurality of thin elongated strips extending between, and connected at their opposed ends to, the circumferentially-closed dome and ring, said strips being of varying radial thickness along their length and having textured outer surfaces; and an elongated plunger having at one end thereof a substantially cylindrical body portion having a diameter essentially equal to the inner diameter of the circumferentially-closed circular ring of the expansion sleeve. When the expansion sleeve is held in a cavity in a bone fragment on one side of a fracture and the plunger is advanced through said circular ring and into the interior of the sleeve with its substantially cylindrical body portion in the leading position, the plurality of thin elongated strips in the sleeve are caused to expand radially outwardly and thereby securely grip the bone fragment. The novel bone implant of this aspect of the invention can be, but is not necessarily, an epiphyseal/metaphyseal implant.

As used herein the topographical term "circumferentially-closed" means that a path can be traced entirely around the circumference of a hollow structure having an axis while avoiding any break or gap or other interruption in the solid material of the structure. Thus, for example, a split ring would not be circumferentially-closed, while a closed ring would be. The uninterrupted path may be irregular in contour but must be continuous for a full 360° with respect to the axis of the structure in question.

Because the expansion sleeve of the bone implant of this aspect of the invention has a smoothly rounded circumferentially-closed dome at its leading end, the likelihood of significant proximal implant migration or "cut-out" in the femoral head is greatly reduced (as compared, for example, to an externally-threaded bone screw or tri-flanged nail). This is a very important feature giving rise to substantially improved product life and substantially reduced bone damage. The feature that the expandable strips in the expansion sleeve extend between, and are connected at their opposed ends to, two circumferentially-closed structures (i.e. the smoothly rounded dome at the leading end of the expansion sleeve and the circular ring at the trailing end) is also significant since it means that these thin strips have no free ends that can contribute to cut-out or catch on the wall of a prepared cavity in the patient's bone structure during implantation. No significant torque (which can cause rotation of the femoral head during insertion or stripping of the bone material) has to be applied to the implant during its implantation, and the radial expansion of the textured strips provides a highly effective and secure bone gripping action distributed along the surface of the sleeve without generating excessive stress concentrations in the bone adjacent the implant. Additionally, because the expandable strips are anchored at both ends fatigue loading is not concentrated at one end of the strip and bending moments are more evenly distributed along the strip. The actuation mechanism of this novel expansion sleeve implant is simple and foolproof and includes no complicated moving parts that might malfunction during implantation. Preferably, the plunger includes a raised annular rib adjacent the trailing end of the plunger body portion, which rib is adapted to fit into a corresponding groove provided in the inner wall of the circular ring of the expansion sleeve when the plunger is fully advanced within the sleeve. This rib and groove combination serves to lock the plunger and sleeve against undesired relative axial displacement after implantation.

It is highly preferred that the expansion sleeve be made of a resilient material such as a titanium-base alloy. In this case, the resilient strips of the expansion sleeve will expand radially outwardly in elastic deformation when the plunger is advanced into the sleeve and will revert to their original shape (to facilitate removal of the sleeve, if desired) when the plunger is withdrawn. Also, whether or not the sleeve is made of a resilient material, it is desirable to design it so that openings are provided in the sleeve in its rest position. An extrudable material such as a bone cement for enhancement of the bone implant fixation can be placed into the sleeve and then extruded through these openings to the bone-implant interface as the plunger is advanced. The desired openings in the sleeve can be distinct gaps between the strips in the rest position of the sleeve, or some other type of opening.

In a preferred surgical implantation technique, a guide wire is placed into the patient's bone at the desired location, a substantially cylindrical cavity to receive the implant is formed with a drill or reamer cannulated to fit over the guide wire, the expansion sleeve is secured (preferably releasably) at its smoothly rounded dome to an elongated cannulated rod (carrying the plunger) which extends within the expansion sleeve and through the circumferentially-closed circular ring thereof, the expansion sleeve is inserted into and held in place within the prepared cavity in the bone by means of the elongated rod (which fits over the guide wire), and the plunger is advanced along said insertion rod into the interior of the expansion sleeve. More preferably, the insertion rod is externally threaded at one end and the dome of the expansion sleeve is provided with a centrally-disposed threaded axial through bore for the releasable attachment of the externally threaded end of the insertion rod.

The present invention also includes a preferred instrument for use in inserting a surgical implant (e.g. the novel expansion sleeve-containing bone implant of the invention discussed above) into a cavity in a patient's bone. This novel insertion instrument comprises an elongated axially cannulated rod having an externally threaded portion adjacent one of its ends and an externally smooth portion extending from the externally threaded portion towards the other end of the rod; a hollow sleeve receiving the elongated rod, which sleeve is capable of sliding movement upon the externally smooth portion of the rod; and means for advancing the hollow sleeve along the externally smooth portion of the elongated rod towards the externally threaded portion of the rod. The sleeve advancing means is preferably structured in such a way that it positively prevents movement of the hollow sleeve along the rod in a direction away from the externally threaded portion of the rod while it is engaged with the sleeve. Suitable sleeve advancing means include a knurled knob threaded upon a second externally threaded portion of the elongated rod on the opposite side of the externally smooth portion than the aforementioned first externally threaded portion, or a spreader tool which interacts with ratchets provided on the elongated rod on said opposite side of its externally smooth portion.

By using the preferred implantation technique and insertion instrument described above, with the hollow sleeve of the instrument positioned behind and forcing the plunger of the implant into the expansion sleeve, the novel expansion sleeve and plunger-containing bone implant of the invention can be readily inserted into the prepared cavity in the patient's bone in a simple surgical procedure involving low consumption of time and minimal risk of surgical error or equipment malfunction and having highly reproducible results from case to case. The same insertion instrument can be used with bone implants of different length. The feature that the sleeve advancing means positively prevents rearward movement of the sleeve along the rod is significant because it permits the surgeon to readily stop advancement of the plunger during its insertion into the expansion sleeve without releasing the compressive force being placed upon the plunger by the hollow sleeve of the insertion instrument.

Another aspect of the present invention is a novel elongated bone plate having an upper surface intended to face away from the patient's bone that is wider than a lower surface intended to face towards the patient's bone, and two side surfaces connecting the upper and lower surfaces which are tapered inwardly toward one another in the direction from the upper surface to the lower surface. The bone plate has a substantially constant thickness between the two side surfaces and is adapted to be secured to a patient's bone by means of bone fasteners received in apertures in the bone plate. Because the lower surface adjacent the bone is thinner (preferably 70% to 90% in width) than the upper surface at which stresses from physiological bending moments applied to the plate tend to be at a maximum, the necessary periosteal tissue stripping adjacent the bone for implantation purposes can be reduced without excessively sacrificing the strength of the bone plate under bending. In one preferred embodiment said upper and lower surfaces are defined in transverse bone plate cross-sections by arcs of two concentric circles, while the two side surfaces are defined therein by two straight radial lines passing through the common center of said concentric circles.

It is also preferred that an elongated bone plate of this aspect of the invention comprise two parallel integral downwardly-extending rails located at opposite sides of the lower surface and extending along substantially the entire length of the bone plate. These two rails serve to lift the lower surface of the bone plate away from the surface of the patient's bone so as to permit enhanced vascularization of the bone directly beneath the lower surface and thus avoid any excessive weakening of that bone tissue.

As has been discussed above in connection with the modular femoral implant kit or system of the invention, it is highly advantageous to provide an elongated bone plate that can be readily connected to the elongated plate portion of another surgical implant in a simple, foolproof, non-time consuming surgical method so as to effectively provide an extension of the length of said elongated plate portion. The other surgical implant may be, for example, another bone plate, an angled side plate, a distal buttress plate, or the like. Thus, a further advantage of the novel elongated bone plate of the invention is that it can be readily connected to a surgical implant having an elongated plate portion adapted to be secured to a patient's bone by means of bone fasteners received in apertures in the elongated plate portion, which plate portion has upper and lower surfaces, with a cavity being formed in the lower surface of the plate portion at a free end thereof, said cavity extending longitudinally from said free end to a shoulder defining an end of the cavity and said cavity having a transverse cross-section complementary to that of the elongated bone plate of the invention. An important consequence of the complementary designs of the transverse cross-sections, including downwardly-inwardly tapered side walls, of the surgical implant cavity and elongated bone plate is that the bone plate "dovetails" with the surgical implant so that it can enter and be removed from the cavity in the surgical implant only by relative axial movement through the cavity opening at the free end of the elongated plate portion of the surgical implant. Also, no relative rotation is permitted between the surgical implant and bone plate. When the end of the bone plate abuts the shoulder at the other end of the cavity, no relative translational movement is possible between the surgical implant and bone plate except for axial separation. By insuring that at least one bone fastener-receiving aperture in the elongated plate portion of the surgical implant overlies a bone fastener-receiving aperture in the bone plate when the plate is inserted into said cavity in the surgical implant and abuts the shoulder at the end of the cavity, a stable and secure assembly of surgical implant and bone plate, in which the length of the elongated plate portion of the surgical implant is effectively extended by the elongated bone plate, can be realized when the assembled surgical implant and bone plate are secured together to the patient's bone.

The present invention comprises additionally a novel distal buttress plate adapted to be secured to the outer cortical wall of the lateral distal femur by means of bone fasteners received in apertures in the plate. The plate includes a relatively flat elongated proximal portion adapted to be secured to the lateral distal femoral shaft and a relatively curved distal portion, curved out of the plane of the proximal portion, adapted to be secured to the lateral distal femoral condyle.

For injuries including a sagital fracture through the distal epiphyseal bone, it is highly desirable to use a distal buttress plate in conjunction with at least two lag screws used for fracture reduction in the distal condylar region, with these lag screws being positioned in close proximity to, but not passing through, the distal portion of the buttress plate. Thus, in accordance with this aspect of the invention, two spaces for the accommodation of a pair of lag screws are left adjacent the sides of a thin neck connecting a wider, generally rounded head at the distal end of said distal portion and a still wider distal portion body having a greater maximum width than the elongated proximal portion of the buttress plate. Preferably, at least one elongated aperture capable of receiving two bone fasteners is provided in the distal portion head and a pair of such elongated apertures, one on each side of the body, are provided in the distal portion body. It is also preferred that the relatively flat proximal portion of the buttress plate be provided with an appropriately dimensioned cavity for a "dovetailed" connection to the novel bone plate of the invention in the manner and for the purposes described above.

Yet another aspect of the present invention is directed to a novel bone implant assembly for the stabilization of a fractured femur comprising an elongated cross-member having a leading portion adapted to be received within a cavity in the femoral head and grip the femoral head and a trailing portion adapted to extend from the leading portion into the intertrochanteric region of a patient's femur, with said trailing portion being provided with a cylindrical through bore, which through bore is at an oblique angle with respect to the longitudinal axis of the cross-member so that it can be brought into approximate alignment with the femoral intramedullary canal when the leading portion of the cross-member is inserted into the femoral head; an intramedullary rod having a distal end portion and a proximal end portion, with the maximum diameter of said proximal end portion being just slightly less than that of the cylindrical through bore in the trailing portion of the elongated cross-member so that said proximal end portion can be received in a close sliding fit within said through bore permitting rotational and translational adjustment of the cross-member with respect to the intramedullary rod; and distinct, positive and active means to releasably lock the elongated cross-member and intramedullary rod to prevent their relative translational and rotational movement when assembled together. The elongated cross-member may be a single integral piece or, alternatively, may comprise two or more non-integral pieces adapted to be connected in use. Thus, for example, the cross-member may comprise a first piece adapted to grip the femoral head and a second piece non-integral therewith adapted to be releasably locked to the intramedullary rod and adapted to receive the first piece in use in an unlocked sliding fit. As used herein, the term "distinct, positive and active means to releasably lock the elongated cross-member and intramedullary rod" refers to one or more structural elements, distinct from the surfaces of the elongated intramedullary rod and the through bore in the cross-member, that are capable of actuation after the intramedullary rod and the cross-member have already been assembled together to effect a positive releasable locking of the intramedullary rod and cross-member. The presence of such releasable locking means, e.g. a locking screw in an internally threaded bore in the cross-member adapted to be screwed so as to firmly press a locking shoe against the proximal end portion of the intramedullary rod, greatly facilitates the obtaining of the precise desired relative disposition of the intramedullary rod and elongated cross-member in a particular clinical case.

Preferably, the elongated intramedullary rod has a circumferentially-closed cross-section and is provided with a plurality of longitudinal splines around its circumference to prevent axial rotation of the implanted rod with respect to the patient's femur and provide enhanced vascularization of bone tissue adjacent the rod outer surface, and the releasable locking means comprises a locking screw and locking shoe held within a bore in the cross-member. The locking shoe has an exterior surface that is complementary to the longitudinally-splined outer surface of the intramedullary rod, and which is pressed against the outer surface of the intramedullary rod when the locking screw is advanced in said bore. More preferably, the elongated cross-member and the intramedullary rod are made of a resilient titanium-base alloy. Most preferably, the intramedullary rod is an extruded hollow body made of Ti-3Al-2.5V alloy.

Additionally, another aspect of the present invention is a novel cancellous or cortical bone screw made of a resilient titanium-base alloy having a head and a partially or fully threaded shank, with an axially-extending recess of generally star-shaped cross-section (e.g. a Torx(TM)-drive or Pozidriv (TM) recess) having substantially parallel axially-extending walls being provided in the screw head for receipt of a driving instrument for the screw. The design of the driving instrument-receiving recess of the novel screw renders the screw far less susceptible to fretting than e.g. a slotted screw, thereby facilitating its insertion into a patient's bone and making practical the use of a resilient titanium-base alloy as the material of construction for the screw.

Other aspects of the present invention will be apparent from a reading of the specification and claims herein in their entirety.

DETAILED DESCRIPTION OF THE INVENTION

The invention will be described in detail with reference to various preferred embodiments thereof. Reference to these embodiments does not limit the scope of the invention, which is limited only by the scope of the claims. In the drawings:

FIG. 1 is an exploded side elevational view of an epiphyseal/metaphyseal implant of the present invention including an expansion sleeve and an elongated plunger;

FIG. 2 is a longitudinal sectional view of the expansion sleeve of the implant of FIG. 1 in the rest position of the sleeve, taken along a plane including the longitudinal axis of the sleeve;

FIG. 2A is an end view of the expansion sleeve of FIG. 1 in the rest position of the sleeve;

FIGS. 3 to 5 are longitudinal sectional views of the implant of FIG. 1, taken along a plane including the common longitudinal axis of the plunger and sleeve, showing three stages in the insertion of the plunger into the sleeve held in a patient's bone;

FIG. 6 is a top plan view of a proximal angled side plate included in a modular implant system or kit of the invention;

FIG. 7 is a sectional view taken along line 7—7 of FIG. 6;

FIG. 8 is a sectional view taken along line 8—8 of FIG. 6;

FIG. 9 is a top plan view of an elongated bone plate included in a modular implant system of the invention;

FIG. 10 is a sectional view taken along line 10—10 of FIG. 9;

FIGS. 11A and 11B are side elevational views of a pair of cortical bone screws of different shank lengths included in a modular implant system of the invention;

FIGS. 12A and 12B are side elevational views of a pair of cancellous bone screws of different shank lengths included in a modular implant system of the invention;

FIG. 13 is an enlarged top plan view of each of the cortical bone screws of FIGS. 11A and 11B;

FIG. 14 is a sectional view taken along line 14—14 of FIG. 9 showing the permitted side-to-side angulation of one of the cortical bone screws of FIG. 11A within one of the bone screw-receiving apertures provided in the bone plate of FIG. 9;

FIG. 15 is a lateral elevational view of the epiphyseal/metaphyseal implant of FIG. 1, the proximal angled side plate of FIG. 6, the elongated bone plate of FIG. 9 and a plurality of cortical bone screws of the type shown in FIGS. 11A and 11B, all connected together and secured to a patient's femur, with the femur shown partly in section;

FIG. 16 is a sectional view taken along line 16—16 of FIG. 15;

FIG. 17 is a sectional view taken along line 17—17 of FIG. 15;

FIG. 18 is a side elevational view of a surgical implant insertion instrument of the invention shown assembled with the expansion sleeve and elongated plunger of the implant of FIG. 1;

FIG. 18A is a sectional view taken along line 18A—18A of FIG. 18;

FIG. 19 is a side elevational view of an intramedullary rod having an anterior-posterior bow included in a modular implant system of the invention;

FIG. 20 is another side elevational view of the intramedullary rod of FIG. 19, as viewed in a direction perpendicular to that of FIG. 19;

FIG. 21 is a sectional view taken along line 21—21 of FIG. 19;

FIG. 22 is a longitudinal view, partially in section, of a proximal end region of an intramedullary rod of the type shown in FIG. 19, illustrating the optional feature of a detachable hollow sleeve secured to the proximal end portion of the intramedullary rod;

FIG. 23 is a top plan exploded view of an elongated intramedullary rod-epiphyseal/metaphyseal implant connection piece, locking screw and locking shoe included in a modular implant system of the invention;

FIG. 24 is a front view, partially in section, of the articles shown in FIG. 23;

Figure 32A:
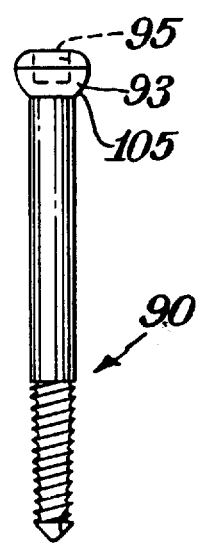
Figure 32B:
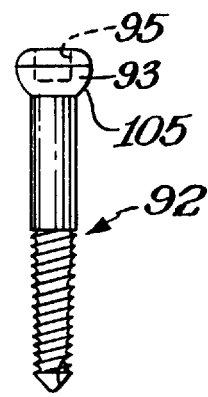

FIG. 25 is an elevational view of an epiphyseal/metaphyseal implant of the type shown in FIG. 1 but of shorter length, the intramedullary rod of FIG. 19 and the connection piece, locking screw and locking shoe of FIG. 23, all connected together and secured to a patient's femur, with the femur shown in section, wherein the epiphyseal/metaphyseal implant and connection piece form together an elongated cross-member;

FIG. 26 is a bottom plan view of a distal angled side plate included in a modular implant system of the invention;

FIG. 27 is a sectional view taken along line 27—27 of FIG. 26;

FIG. 28 is an elevational view of an epiphyseal/metaphyseal implant of the type shown in FIG. 1 but of shorter length, the distal angled side plate of FIG. 26, the elongated bone plate of FIG. 9 and a plurality of cortical bone screws of the type shown in FIGS. 11A and 11B, all connected together and secured to a patient's femur, with the femur shown in section;

FIG. 29 is a top plan view of a distal buttress plate included in a modular implant system of the invention;

FIG. 30 is a side elevational view of the distal buttress plate of FIG. 29;

FIG. 31 is an elevational view of the distal buttress plate of FIG. 29, the elongated bone plate of FIG. 9 and a plurality of cortical and cancellous bone screws of the type shown in FIGS. 11A, 11B, 12A and 12B, all connected together and secured to a patient's distal femur, with the femur shown in section; and FIGS. 32A and 32B are side elevational views of a pair of cortical bone screws of different shaft lengths suitable for use as distal locking screws.

Except as otherwise indicated, all of the implants shown in FIGS. 1 to 32B depicting various preferred embodiments of the invention are made of a resilient, physiologically-inert titanium-base alloy.

An elongated epiphyseal/metaphyseal implant 1 of the invention is shown in FIG. 1. Implant 1 comprises an integral substantially cylindrical expansion sleeve 3 and an elongated plunger 5. Sleeve 3 includes a smoothly rounded circumferentially-closed dome 7 at one end, a circumferentially-closed circular ring 9 at the opposite end, and a plurality (eight in the embodiment shown in FIGS. 1 to 5) of identical substantially straight elongated thin resilient strips 11 extending between, and connected at their opposed ends by and to, dome 7 and ring 9. A centrally-disposed threaded axial through bore 15 is provided in dome 7 for releasably securing an elongated insertion rod to the dome. Strips 11 have textured outer surfaces to enhance the bone-gripping action of the implant and define together the cylindrical wall of sleeve 3, which sleeve wall has in the rest position of the sleeve an outer diameter essentially equal to the outer diameter of ring 9. As is shown in FIG. 2, each of the strips 11 is of varying thickness along its length so that the sleeve wall has in the rest position of the sleeve an inner diameter in a region $r_1$ adjacent ring 9 equal to the inner diameter of ring 9 and an inner diameter in a region $r_2$ spaced from ring 9 reduced from the inner diameter of ring 9. The strips 11 do not touch each other along their lengths in the rest position of the sleeve, but are instead separated by an equal number of longitudinal openings, e.g. 13.

Plunger 5 includes at one end thereof a substantially cylindrical body portion 17 having a diameter essentially equal to the inner diameter of ring 9 of sleeve 3, and a cylindrical stem portion 19 having a smaller diameter than body portion 17 extending from body portion 17 to the other end of the plunger. Plunger 5 is cannulated along its longitudinal axis, as shown in FIG. 1. An internally threaded recess 20 is provided at the trailing end of stem portion 19 for engagement with an externally threaded tool to remove plunger 5 from the patient's bone after implantation, if desired.

The body portion 17 of plunger 5 includes a raised annular lip 18 adjacent the trailing end of portion 17, a groove 10 is provided in the inner wall of ring 9 and a plurality (eight in the embodiment shown in FIGS. 1 to 5) of relatively short slots 12 (open at the trailing edge of ring 9) are provided in the closed ring 9, all for a purpose to be described below.

FIGS. 3 to 5 show how bone implant 1 is actuated to grip a patient's bone B at the leading end portion of the implant. The expansion sleeve 3 is inserted into and held within a cylindrical cavity C in the patient's bone B by means of an insertion rod 21 having an externally threaded end portion 23 screwed into the internally threaded bore 15 of sleeve 3. Insertion rod 21 extends along the longitudinal axis of sleeve 3 and is cannulated to fit over a guide wire 25. Cannulated plunger 5, which is in a sliding fit over rod 21, is advanced along rod 21 towards sleeve 3 (i.e. from left to right in FIG. 3) with its substantially cylindrical body portion 17 in the leading position. After the body portion 17 of plunger 5 first contacts the elongated strips 11 at the beginning of region $r_2$ (see FIG. 4), the continued advancement of plunger 5 into the interior of sleeve 3 causes the eight strips 11 to expand radially outwardly against the wall of the cavity C and securely grip the patient's bone B. When the plunger 5 is fully advanced within the expansion sleeve 3 (see FIG. 5), the raised lip 18 fits into the groove 10 to lock the sleeve 3 and plunger 5 against an undesired axial disengagement after implantation of the implant 1. The equally-spaced (circumferentially) slots 12 impart a slight resiliency to the ring 9 which allows the rib 18 to snap into the groove 10. Additionally, when the plunger is fully advanced within the sleeve, the cylindrical wall of the sleeve 3 has taken on a generally barrel-shaped contour, which results from the fact that the opposite ends of each strip 11 are fixed to dome 7 and ring 9, respectively. Since the expansion sleeve 3 is made of a resilient material the strips 11 expand radially outwardly in elastic deformation when the plunger 5 is fully advanced into the expansion sleeve 3. If desired, an extrudable bone cement or bone filler material can be inserted into the sleeve 3 so that when the plunger 5 is advanced into the sleeve 3 the bone cement or bone filler is extruded through the openings 13 to the sleeve-bone interface.

An insertion instrument 27 of the invention for use in the implantation of bone implant 1 is shown in FIG. 18 assembled with sleeve 3 and plunger 5. Insertion instrument 27 includes the elongated axially-cannulated insertion rod 21 (upon which plunger 5 can slide) having an externally threaded end portion 23 adapted to be screwed into threaded bore 15 in dome 7 of sleeve 3 and an externally smooth portion 29 extending from the threaded portion 23, a hollow sleeve 31 capable of sliding movement upon smooth portion 29, a handle 33 and a means 35 for advancing the hollow sleeve 31 along the smooth portion 29 of rod 21 towards the externally threaded portion 23 of rod 21. The sleeve advancing means 35 comprises a knurled knob 37 threaded upon an externally threaded portion 39 of the elongated rod 21. As knob 37 is turned it pushes against sleeve 31. Preferably, a nylon washer (not shown in the figures) is fitted between knob 37 and sleeve 31. A guide pin 41 provided on the inner wall of sleeve 31 is received within a longitudinal groove provided in threaded portion 39 (see FIG. 18A). In use, the surgeon holds handle 33 in one hand and turns knob 37 with the other hand to advance hollow sleeve 31 toward the expansion sleeve 3. The hollow sleeve 31 abuts the plunger 5, which is also fitted on the insertion rod 21, and thus in turn forces plunger 5 along the rod until the plunger is advanced into the expansion sleeve 3. As the cylindrical body portion 17 of the plunger 5 is being pressed by knob 37 and hollow sleeve 31 against the elongated strips 11 of the expansion sleeve 5 and forcing the strips 11 to expand, the surgeon can stop advancement of the plunger into the expansion sleeve (to rest, to assess the surgical situation, or for any other reason) without relaxing the force being placed on the plunger by the insertion instrument 27. In such a situation movement of hollow sleeve 31 and plunger 5 along insertion rod 21 away from expansion sleeve 5 is positively prevented by the structure of the sleeve advancing means 35.

After the implantation of the expansion sleeve 3 and the plunger 5 has been completed, with the plunger fully advanced within the interior of the sleeve, the guide wire 25 and the insertion rod 21 are removed from the patient's bone, although it is contemplated that an appropriately dimensioned insertion rod and/or guide wire might be left in place in the patient's bone to form a part of the implanted elongated bone implant.

A proximal angled side plate 43 which may be included in a modular implant system or kit of the invention is shown in FIGS. 6 and 7. Proximal angled side plate 43 includes an elongated plate portion 45 adapted to be secured to the outer cortical wall of the femoral shaft and an integral hollow sleeve 47 extending from one end of plate portion 45. The elongated plate portion 45 has an upper surface 49 and a lower surface 51 intended to be adjacent the patient's bone in use, while the hollow sleeve 47 is provided with a longitudinal cylindrical through bore 53 extending from upper surface 49 to the free end of hollow sleeve 47. As shown in FIG. 7, the elongated plate portion 45 and hollow sleeve 47 are oriented at an oblique angle of about 130°–150° so that hollow sleeve 47 is adapted to extend into the intertrochanteric region of the femur when elongated plate portion 45 is secured to the outer cortical wall of the adjacent femoral shaft.

As used herein, the term "adapted to be secured to the outer cortical wall" of a bone (e.g. a femur) means that an implant is adapted to be secured to a bone in such a way that it abuts the outer cortical wall of the bone. As one example, an implant may be provided with a plurality of apertures along its length for the receipt of bone fasteners (e.g. bone screws, nails, pins, bolts, rivets, or the like) used to secure the implant to the outer cortical wall.

As is shown in FIGS. 6 and 7, three circular through apertures 55, 57 and 59 are provided in the elongated plate portion 45 of the proximal angled side plate 43 for the receipt of three bone screws, one in each aperture. These three apertures are staggered with respect to the longitudinal axis of plate portion 45 (see FIG. 6) in order to reduce stress concentrations in the secured plate portion and in the bone. As shown in FIG. 7, the upper portions 61 of the walls of apertures 55, 57 and 59 adjacent upper surface 49 are preferably identical, concave-upward spherical surfaces. These identical spherical surfaces are adapted for cooperation with spherically-headed cortical and cancellous bone screws, as is discussed below. Two of these apertures, 57 and 59, communicate with an elongated cavity 63 formed in the lower surface 51 of plate portion 45, which cavity extends longitudinally from the free end 65 of plate portion 45 to a shoulder 67. Cavity 63 is adapted to receive an end portion of an elongated bone plate of the invention in a sliding fit, as will be described below. The lower surface 51 of elongated plate portion 45 is slightly curved (as viewed in transverse cross-sections of plate portion 45 (see FIG. 8)) to conform to the outer cortical wall of a femur.

An elongated bone plate 69 of the invention adapted to be secured to a patient's bone is shown in FIGS. 9 and 10. Bone plate 69 has an upper surface 71, a lower surface 73 intended to be adjacent the patient's bone in use and two side surfaces 75 and 77 connecting surfaces 71 and 73. Bone plate 69 is provided with for example six identical elongated through apertures, e.g. 79, 80 and 85, for the receipt of bone screws used to secure the plate to a patient's bone, e.g. to the outer cortical wall of the femoral shaft. Some other number (odd or even) of elongated through apertures than six may be provided in the bone plate of the invention, if desired. Preferably, the elongated apertures are alternately offset from the longitudinal axis of the bone plate (see FIG. 9) in order to reduce stress concentrations in the secured bone plate and in the bone and the separation between the two centermost slots (e.g. the third and fourth slots in FIG. 9) is greater than the separation between other pairs of adjacent slots. As can be readily seen in FIG. 10, the width of upper surface 71 is greater than the width of lower surface 73, side surfaces 75 and 77 are tapered inwardly toward one another in the direction from surface 71 to surface 73 (i.e. downwardly and inwardly in FIG. 10), and the thickness T of the bone plate 69 is substantially constant across the bone plate from side surface 75 to side surface 77. In the embodiment of FIGS. 9 and 10, bone plate 69 includes two parallel rails 81 and 83 located at the opposite sides of lower surface 73, which rails extend along substantially the entire length of plate 69. In use, only rails 81 and 83 contact the surface of the patient's bone to minimize interference with bone or periosteal vascularity.

An important feature of bone plate 69 is that its transverse cross-sectional dimensions are complementary to those of the cavity 63 in the elongated plate portion 45 of the proximal angled side plate 43. Thus, either end of bone plate 69 can be inserted into cavity 63, but because of the tapered side surfaces of the bone plate and cavity the bone plate 69 can enter and be removed from the cavity 63 only by relative axial movement through the opening of cavity 63 at the free end 65 of plate portion 45. Separation or joining by relative movement in the vertical direction is not permitted and the bone plate 69 cannot rotate with respect to the proximal angled side plate 43 when it is inserted within the cavity 63 (see FIG. 17 for a depiction of the "dovetail" interlock between plate portion 45 and bone plate 69). When either end of bone plate 69 is inserted into cavity 63 and the end of the bone plate abuts shoulder 67, apertures 57 and 59 in the angled side plate 43 overlie apertures 79 and 85, respectively, in the bone plate 69. Thus, with the use of two bone screws passed through the two overlying pairs of apertures and threaded into the patient's bone, bone plate 69 can be secured to the elongated plate portion 45 of side plate 43 in axial alignment in a stable and secure connection so as to provide an effective extension of the length of plate portion 45 in vivo.

In a preferred modular system of the invention three bone plates of varying length of the type shown in FIG. 9 are provided, having four, six and eight elongated apertures respectively, for use either independently or to extend the length of side plates.

Elongated bone plate 69 may also be used by itself as a conventional bone plate in the treatment of, for example, diaphyseal femoral fractures. The six apertures in the plate are elongated to be able to receive either one or two screws each in use. Preferably, the upper portions 107, adjacent upper surface 71, of the identical apertures are spherically-rounded concave-upward all the way around the aperture. These identical spherically-rounded surfaces are adapted for cooperation with spherically-headed cortical and cancellous bone screws, as is discussed below.

Bone plate 69 is preferably slightly curved (as viewed in transverse cross-sections such as FIG. 10) to conform to the shape of the human femoral shaft. In the preferred embodiment shown in FIG. 10, upper surface 71 and lower surface 73 are defined in transverse bone plate cross-sections by arcs of two concentric circles having a center O, while side surfaces 75 and 77 are defined by two straight lines which, when extended, pass through center O and form together an angle A.

A pair of self-tapping cortical bone screws 89 and 91 which may be included in a modular implant system of the invention are shown in FIGS. 11A and 11B. Screws 89 and 91 have identical heads 93 and identical shanks 97 and 99 externally threaded along essentially the entire shank length, with the single exception that shank 97 of screw 89 is longer than shank 99 of screw 91. A pair of self-tapping cancellous bone screws 101 and 103 which may be included in a modular implant system of the invention are shown in FIGS. 12A and 12B. The heads 93 of screws 101 and 103 are identical to the heads of cortical screws 89 and 91, while the shanks of cancellous screws 101 and 103, which are externally threaded adjacent the free shank end only, are identical with the single exception that the shank of screw 101 has a longer unthreaded portion than the shank of screw 103. Another pair of self-tapping cortical bone screws 90 and 92 are shown in FIGS. 32 and 32A. These screws are identical to screws 89 and 91 except that a portion of the shanks of screws 90 and 92 is not threaded. As is shown in FIG. 13, an identical axially-extending recess 95 having parallel axially-extending walls is provided in each of the identical heads 93 of screws 89, 91, 90, 92, 101 and 103 for the receipt of a screw-driving instrument (e.g. a screwdriver). The recess is generally star-shaped in cross-section, e.g. the generally star-shaped Torx (TM)-drive cross-section shown in FIG. 13 or the generally star-shaped cross-section of a Pozidriv (TM) recess. If desired, the cortical and/or cancellous bone screws may be reduced in one or more steps in diameter or tapered towards the free shank end for increasing grip strength on the neighboring femoral cortex.

Another important feature of the design of screw head 93 is that the underside 105 of head 93 is spherically-rounded and substantially complementary with the spherically-rounded upper portions of the walls of the screw-receiving apertures in angled side plate 43 and elongated bone plate 69. FIG. 14 shows the permitted side-to-side angulation of one of the four screws of FIGS. 11A, 11B, 12A and 12B (shown in phantom lines) within one of the screw-receiving apertures (i.e. aperture 80) provided in the bone plate 69. As a consequence of the substantially complementary spherically-rounded surfaces of head underside 105 and the upper portion 107 of the wall of aperture 80, screw 89 is capable of rotating through an angle of about 30° in a plane perpendicular to the longitudinal axis of bone plate 69. Essentially unrestricted angulation is permitted in a plane parallel to the longitudinal axis of the bone plate. However, when bone screw 89 is positioned fully at the end of aperture 80 unrestricted angulation is permitted in one direction only in a plane parallel to the longitudinal axis of the bone plate while only about a 15° rotation from the vertical is permitted in the opposite direction in said plane. The radius of the spherically-rounded surface of the upper portion 61 of the apertures 55, 57 and 59 in the angled side plate 43 is equal to the radius in the transverse plane of FIG. 14 of the surface of the upper portion 107 of aperture 80 of bone plate 69. Thus, screws 89, 91, 101 and 103 are capable of a universal rotation with respect to the elongated plate portion 45 within a cone having an apex angle of about 30° when fully advanced within one of the apertures 55, 57 and 59. (However, when the angled side plate is connected with an elongated bone plate this freedom of rotation is restricted considerably for the two screws passing through both plates.) The substantial allowed angulation of bone screws within an elongated bone plate or angled side plate enhances capabilities for adaptation to the fixation of oblique fractures and complex fracture patterns such as butterfly fractures. This angulation permits the bone screws to extend approximately normally to many fracture lines and serves to increase the number of bone fragments that can be directly gripped by at least one screw.

Elongated epiphyseal/metaphyseal implant 1, proximal angled side plate 43, elongated bone plate 70 having four elongated apertures and a plurality of the cortical bone screws 89 can be connected together and secured to a patient's right femur F in the manner shown in FIGS. 15 to 17 to form an angled side plate-hip pin assembly with the effective length of the elongated plate portion of the angled side plate extended by the elongated bone plate. The implant 1 is first implanted within a cavity prepared in the proximal femur, which cavity must be widened adjacent its open end to accommodate hollow sleeve 47, said sleeve 47 of side plate 43 is then inserted into the cavity so that a portion of the cylindrical stem portion 19 of plunger 5 is received in a sliding fit within the cylindrical bore 53 of sleeve 47, one end of bone plate 70 is slid into cavity 63 of side plate 43 until it abuts shoulder 67, and the entire assembly is then secured to the femur F with a plurality of cortical bone screws 89 passed through apertures in side plate 43 and bone plate 70. If desired, one or more conventional fixation pins (e.g. Knowles pins) unconnected to implant 1 and angled side plate 43 may also be implanted, with an orientation substantially parallel to the orientation of implant 1 shown in FIG. 16. Bone plate 70 can, of course, be omitted from the assembly of FIG. 16 if the length of plate portion 45 is sufficient without extension in a particular surgical situation.

A femoral intramedullary rod 109 which may be included in a modular implant system or kit of the invention is shown in side elevational views in FIGS. 19 and 20 as viewed in perpendicular directions. Rod 109 has a proximal end 111 and a distal end 113 and a pair of transverse through bores 115 adjacent distal end 113 to receive bone screws 90. One or two through bores 116 to receive locking bone screws may also be included adjacent proximal end 111. Rod 109 has a distal end portion 117 and a straight proximal end portion 119. As is shown in FIG. 19, rod 109 has a slight bow, which is intended to lie in the anterior-posterior plane of the femur after implantation; no such bow is exhibited in FIG. 20, since rod 109 is intended to be straight in the lateral-medial plane after implantation. The transverse cross-section of rod 109 is shown in FIG. 21. This cross-section has a closed profile, with the outer periphery of the cross-section being a plurality of (e.g. six) smoothly rounded peaks (e.g. 121), all terminating on the same first circle, connected by an equal number of smoothly rounded valleys (e.g. 123), all bottoming on the same second circle concentric with and of smaller diameter than said first circle. The provision of these alternating peaks and valleys greatly enhances the stability of the implanted rod 109 against axial rotation with respect to the patient's bone, while their smoothly rounded nature greatly reduces the possibilities for damaging the bone of the intramedullary wall. Furthermore, the alternately raised and lowered outer peripheral rod configuration shown in FIG. 21 provides for extensive re-vascularization of the bone tissue of the intramedullary canal wall following reaming. FIG. 21 also shows that rod 109 is axially cannulated, with an axial bore 125 extending from the distal tip 127 of hollow rod 109 to the proximal tip 129 of the rod. A diametrical slot 120 is provided at proximal tip 129 for engagement with appropriate insertion and extraction tools.

An elongated connection piece 139, locking screw 141 and locking shoe 142 for connecting an epiphyseal/metaphyseal implant 1 to intramedullary rod 109 adjacent to the proximal end 111 of rod 109 to form a Y-nail type of assembly are shown in FIGS. 23 and 24. Connection piece 139 is provided at one end with an elongated cylindrical cavity 143 aligned with the longitudinal axis of piece 139 and adapted to receive the free end of stem portion 19 of plunger 5 of implant 1 in a sliding fit. Connection piece 139 is also provided with a cylindrical through bore 145 disposed at an oblique angle of about 135° with respect to said longitudinal axis, and an elongated partially countersunk and partially internally-threaded bore 147 aligned with said longitudinal axis at the end of the elongated connection piece 139 opposite to cavity 143. Bore 147 is adapted to receive locking screw 141 and locking shoe 142, and both bore 147 and cavity 143 open into through bore 145. The diameter of through bore 145 is just slightly greater than that of the maximum cross-sectional dimension of the proximal end portion 119 of intramedullary rod 109 so that proximal end portion 119 can be received in a close sliding fit within through bore 145 permitting rotational and translational adjustment of the connection piece 139 with respect to the intramedullary rod 109. Connection piece 139 and intramedullary rod 109 can be securely locked against relative translational and rotational movement by screwing locking screw 141 forward in the partially threaded bore 147 behind the locking shoe 142 until the leading surface 144 of locking shoe 142 very firmly presses against the surface of proximal end portion 119, and then unlocked again if desired simply by unscrewing screw 141. The leading surface 144 of locking shoe 142 has a grooved contour adapted to fit closely and mesh with the splined external contour of rod 109, thereby enhancing the secure locking of rod 109 to the connection piece 139. Locking screw 141 and locking shoe 142 are assembled together in use, e.g. by a captured thread or staked head connection, to cause withdrawl of shoe 142 when screw 141 is unscrewed while permitting independent relative rotation between these two element during screwing and unscrewing of screw 141.

In the alternative embodiment shown in FIG. 22, a hollow sleeve 131 having a smooth cylindrical outer surface is detachably secured to the exterior of the proximal end portion 119 of intramedullary rod 109 (having the fluted cross-section of FIG. 21) by means of a locking screw 135 having a head and an externally threaded shank fitted through a centrally-disposed opening in the top wall of sleeve 131 and threaded into an internally-threaded centrally-disposed bore 137 at the top of rod 109. An advantage of the embodiment of FIG. 22 is that the diameter of the straight proximal end of rod 109 is effectively increased above that of the maximum transverse dimension in the transverse cross-section of FIG. 21. The hollow sleeve 131 should extend distally at least to the point of maximum applied bending moment in normal use, which point of maximum bending moment is usually in the subtrochanteric region of the femur, but not all the way to the midway point along the length of rod 109 between the distal and proximal tips 127 and 129 of the rod. When hollow sleeve 131 is used, the contour of the leading surface of locking shoe 142 should be adapted accordingly, or alternatively, the locking shoe can be eliminated and the locking screw used alone.

Intramedullary rod 109, connection piece 139, locking screw 141, locking shoe 142 and a bone implant 1 can be connected together in the manner shown in FIG. 25 to form a Y-nail type of assembly in a femur F, with implant 1 and piece 139 forming together the elongated cross-member of the Y-nail. The epiphyseal/metaphyseal implant 1 is first implanted into a cavity prepared in the proximal femur, which cavity must be widened adjacent its open end to accommodate the connection piece 139. Piece 139 is then advanced into the prepared bone cavity and oriented so that a portion of stem portion 19 of plunger 5 is received in a sliding fit within cavity 143 and through bore 145 is in approximate alignment with the femoral intramedullary canal. Rod 109 is advanced distally through an opening prepared by conventional means in the proximal femur wall and through the through bore 145 in piece 139 until the distal end portion 117 of rod 109 is in the distal femur and the proximal end portion 119 of the rod 109 is within the through bore 145. The disposition of rod 109 with respect to the femur F and connection piece 139 is then carefully adjusted to the desired disposition, and connection piece 139 is then locked to intramedullary rod 109 by means of the locking screw 141 and locking shoe 142. If desired a cortical bone screw 90 of the type shown in FIG. 32A of large shank length can be inserted by conventional methods through one or both of the transverse bores 115 to lock the rod 109 to the distal femur. Also, cap screw 135 may be screwed into bore 137, even when sleeve 131 is not being used, to prevent bone ingrowth into the threads in bore 137.

It is contemplated that a connection piece similar to piece 139 could be used, if desired, to connect an epiphyseal/metaphyseal implant similar to implant 1 to the distal end portion 117 of intramedullary rod 109, with the epiphyseal/metaphyseal implant residing in the distal condylar region of the femur and being substantially perpendicular to said portion 117. In such a case the through bore of the connection piece analogous to through bore 145 in piece 139 would be substantially perpendicular to the longitudinal axis of the connection piece.

A distal angled side plate 149 which may be included in a modular implant system or kit of the invention is shown in FIGS. 26 and 27. Distal angled side plate 149 includes an elongated plate portion 151 adapted to be secured to the outer cortical wall of the distal femoral shaft and an integral hollow sleeve 153 extending from one end of plate portion 151. As is shown in FIG. 27, the plate portion 151 is slightly angulated in the vicinity of line R in order to accommodate the commencement of the anatomical bulge of the lateral distal femur. The elongated plate portion 151 has an upper surface 155 and a lower surface 157 intended to be adjacent the patient's bone in use, while the hollow sleeve 153 is provided with a longitudinal cylindrical through bore 159 extending from upper surface 155 to the free end of hollow sleeve 153. As shown in FIG. 27, the elongated plate portion 151 and hollow sleeve 153 are substantially perpendicular so that hollow sleeve 153 is adapted to extend into the distal condylar region of the femur when elongated plate portion 151 is secured to the outer cortical wall of the adjacent distal femoral shaft. Through bore 159 is dimensioned to receive a portion of the stem portion 19 of the plunger 5 of an elongated epiphyseal/metaphyseal implant 1 in a sliding fit. The lower surface 157 is slightly curved in transverse cross-section in a similar manner as shown in FIG. 8 (for the proximal side plate 43) to conform to the outer cortical wall of a distal femur.

Three circular through apertures 161, 163 and 165 are provided in plate portion 151 for the receipt of three bone screws (e.g. cortical screw 89), one in each aperture. These three apertures are staggered with respect to the longitudinal axis of plate portion 151 (see FIG. 26) in order to reduce stress concentrations in the secured plate portion and in the bone. Apertures 161, 163 and 165 are identical respectively to apertures 55, 57 and 59 in the proximal angled side plate 43. The distal angled side plate 149 is also provided with an elongated cavity 167 formed in the lower surface 157 of plate portion 151. Cavity 167 is identical to cavity 63 in the proximal angled side plate 43. Thus, cavity 167 is adapted to receive either end of elongated bone plate 69 in a "dovetail" interlocked sliding fit (see FIG. 17), and when the end of the bone plate abuts shoulder 169 apertures 163 and 165 overlie the two terminal apertures, e.g. apertures 79 and 85 respectively, in the bone plate 69.

The distal angled side plate 149, an elongated epiphyseal/metaphyseal implant 1 and a plurality of the cortical bone screws 89 can be connected together and secured to a patient's femur F in the manner shown in FIG. 28 to form a distal side plate-pin assembly with the effective length of the elongated plate portion of the side plate extended by the elongated bone plate. The preferred surgical procedure is analogous to the one described above with regard to the assembly of FIGS. 15 and 16. Bone plate 69 can, of course, be omitted from the assembly of FIG. 28 if the length of plate portion 151 is sufficient without extension in a particular surgical situation.

A distal buttress plate 171 of the invention adapted to be secured to the outer cortical wall of the lateral distal femur is shown in FIGS. 29 and 30. Buttress plate 171 includes a relatively flat elongated proximal portion 173 adapted to be secured to the lateral distal femoral shaft and a three dimensionally-contoured distal portion 175 designed to replicate the mean geometry of the lateral femoral condyle of adult humans. The distal portion 175 includes a generally rounded head 177 at the distal end of plate 171, a generally widened body 179 having a greater maximum width than both head 177 and proximal portion 173, and a neck 181 having a minimum width W substantially smaller than the maximum widths of head 177 and body 179. As viewed in transverse cross-sections, the lower surface of the distal buttress plate 171 is contoured along its entire length to conform to the outer cortical wall of the distal femur.

Distal buttress plate 171 is adapted to be secured to the outer cortical wall of the lateral distal femur by means of bone screws received in apertures in the plate. Thus, three circular through apertures 183, 185 and 187 are provided in proximal portion 173 for the receipt of three bone screws (e.g. cortical screw 89), one in each aperture. These three apertures are staggered with respect to the longitudinal axis of proximal portion 173 (see FIG. 29), and are identical respectively to apertures 55, 57 and 59 in the angled side plate 43. Also, an elongated aperture 189 is provided in head 177 and two elongated apertures 191 and 193 are provided in body 179, one on each side of body 179. Each of apertures 189, 191 and 193 is substantially identical to the apertures in the elongated bone plate 69 and thus are each configured to receive two (or one, if only one is desired) bone screws having a head 93 and permit the universal angulation of said screws when fully advanced in the aperture.

Furthermore, it is often highly desirable to use a distal buttress plate in conjunction with a pair of fracture reduction lag screws extending across the distal condylar region of the femur. Such lag screws are screwed fully into the bone before the distal buttress plate is implanted and thus cannot practically be passed through the plate. An important feature of distal buttress plate 171 is that the distal portion 175 thereof is configured in such a manner that spaces outside the periphery of plate 171 are left against neck 181 for the accommodation of two fracture reduction lag screws, extending across the distal condylar region of the femur, on the two sides of neck 181. These two lag screws are shown in phantom in FIG. 29 as elements 195 and 197.

Finally, the distal buttress plate 171 is also provided with an elongated cavity 199 formed in the lower surface of the proximal portion 173. Cavity 199 is identical to, and is adapted to serve in the same bone plate-"dovetail" interlocking capacity as, cavity 63 in the angled side plate 43 and cavity 167 in the angled side plate 149. When the end of bone plate 69 inserted into cavity 199 abuts the shoulder 201 of the cavity, apertures 185 and 187 overlie the two terminal apertures, e.g. apertures 79 and 85 respectively, in the bone plate 69.

Distal buttress plate 171, elongated bone plate 69, a plurality of cortical bone screws such as screw 89 and a plurality of cancellous bone screws such as screw 101 can be connected together and secured to a patient's femur F in the manner shown in FIG. 31. First, two lag screws (not shown in FIG. 31) are fully implanted in the distal condylar region, if desired, to reduce a fracture in said region. These implanted lag screws are positioned so that they lie generally in the lateral-medial plane and are spaced so that they will lie in close proximity to the two opposite sides of the neck 181 of portion 175 (see FIG. 29). The distal buttress plate 171 is then secured to the lateral femur, with neck 181 fitting between the two previously implanted fracture reduction lag screws, by means of bone screws 101 passing through apertures 189, 191 and 193 (one or two screws can be passed through each of apertures 189, 191 and 193, as desired) and a bone screw 89 passed through aperture 183. Bone plate 69 is then slid into cavity 199 until its end abuts shoulder 201 and bone screws 89 are screwed to the femur F through apertures 185 and 187. Finally, bone screws 89 are screwed to the femur F through some or all of the four apertures of bone plate 69 remaining outside of the cavity 199. Distal buttress plate 171 can, of course, be implanted without bone plate 69 if the length of the proximal portion 173 is sufficient without extension for a particular surgical situation.

We claim:

1. An elongated plate adapted to be secured to a patient's bone, said plate having an upper surface, a lower surface intended to be adjacent the patient's bone in use and two side surfaces connecting the upper and lower surfaces, wherein said upper and lower surfaces are defined in transverse bone plate cross-sections by arcs of two concentric circles and said two side surfaces are defined therein by two straight lines which, when extended, form an angle bisected by a diametrical line of said concentric circles, said plate comprising two parallel integral rails extending downwardly along substantially the entire length of the plate, with said rails being located at opposite sides of said lower surface, whereby only said rails contact the patient's bone when the bone plate is secured thereto, with the thickness of the plate being substantially constant between the two side surfaces at positions where no apertures and no rails are present, the width of the upper surface being greater than the width of the lower surface, said side surfaces being tapered inwardly toward one another from said upper surface to said lower surface, said sides surfaces forming acute angles with said upper surface and said side surfaces forming obtuse angles with said bottom surface, with said bone plate being adapted to be secured to the patient's bone by means of bone fasteners received in apertures in the bone plate.

2. An elongated bone plate of claim 1 made of a resilient titanium-base alloy.

3. An apparatus comprising an elongated bone plate of claim 1 and including also bone fasteners to be received in apertures in said bone plate.

4. An elongated bone plate of claim 1, wherein the lower surface adapted to be positioned adjacent the bone is 70% to 90% thinner in width than the upper surface at which stresses from physiological bending moments applied to the plate tend to be at a maximum.

5. A method of treating a fractured human femoral bone shaft of a patient, while reducing any necessary periosteal tissue stripping adjacent said bone for implantation purposes and while simultaneously permitting enhanced vascularization of said bone and thus avoiding any excessive weakening of said bone, said method comprising:

(a) stripping a minimal amount of periosteal tissue from said bone;

(b) positioning adjacent to said patient's bone an elongated bone plate, said bone plate having an upper surface, a lower surface intended to be positioned adjacent the patient's bone in use, and two side surfaces connecting the upper and lower surfaces, wherein said upper and lower surfaces are defined in transverse bone plate cross-sections by arcs of two concentric circles and said two side surfaces are defined therein by two straight lines which, when extended, form an angle bisected by a diametrical line of said concentric circles, said plate comprising two parallel integral rails extending downwardly along substantially the entire length of the plate, with said rails being located at opposite sides of said lower surface, whereby only said rails contact the patient's bone when the bone plate is secured thereto, with the thickness of the plate being substantially constant between the two side surfaces at positions where no apertures and no rails are present, the width of the upper surface being greater than the width of the lower surface, said side surfaces being tapered inwardly toward one another from said upper surface to said lower surface, said side surfaces forming acute angles with said upper surface and said side surfaces forming obtuse angles with said bottom surface, with said bone plate being adapted to be secured to the patient's bone by means of bone fasteners received in apertures in the bone plate; and (c) securing said elongated bone plate to the patient's bone by means of bone fasteners received in apertures in the bone plate.

* * * * *